United States Patent
Haddleton et al.

(10) Patent No.: US 12,128,142 B2
(45) Date of Patent: Oct. 29, 2024

(54) PATCH

(71) Applicant: MEDHERANT LTD, Coventry (GB)

(72) Inventors: David Haddleton, Kenilworth (GB); Gabit Nurumbetov, Coventry (GB); Andrew Ross, Grendon (GB); Vasiliki Nikolaou, Coventry (GB)

(73) Assignee: MEDHERANT LTD, Coventry (GB)

( * ) Notice: Subject to any disclaimer, the term of this patent is extended or adjusted under 35 U.S.C. 154(b) by 153 days.

(21) Appl. No.: 17/260,952

(22) PCT Filed: Jul. 18, 2019

(86) PCT No.: PCT/GB2019/052003
§ 371 (c)(1),
(2) Date: Jan. 15, 2021

(87) PCT Pub. No.: WO2020/016581
PCT Pub. Date: Jan. 23, 2020

(65) Prior Publication Data
US 2021/0283067 A1   Sep. 16, 2021

(30) Foreign Application Priority Data
Jul. 19, 2018 (GB) ..................................... 1811834

(51) Int. Cl.
*A61K 9/70* (2006.01)
*A61K 31/167* (2006.01)
(Continued)

(52) U.S. Cl.
CPC .......... *A61K 9/7069* (2013.01); *A61K 9/7053* (2013.01); *A61K 31/167* (2013.01); *A61K 31/192* (2013.01); *A61K 31/465* (2013.01)

(58) Field of Classification Search
CPC .. A61K 9/7069; A61K 9/7053; A61K 31/167; A61K 31/192; A61K 31/465
See application file for complete search history.

(56) References Cited

U.S. PATENT DOCUMENTS

| 8,378,037 B2 | 2/2013 | Griswold |
| 2002/0013442 A1 | 1/2002 | Sherman et al. |

(Continued)

FOREIGN PATENT DOCUMENTS

| CA | 2217979 A1 | 10/1996 |
| EP | 0822952 | 2/1998 |

(Continued)

OTHER PUBLICATIONS

Silverman, "The Organic Chemistry of Drug Design and Drug Action", p. 19-21, 1992. (Year: 1992).*

(Continued)

*Primary Examiner* — Jianfeng Song
(74) *Attorney, Agent, or Firm* — SNELL & WILMER L.L.P.

(57) ABSTRACT

The invention relates to novel compositions comprising urea and amine functionalised silyl containing polymers which, in combination with tackifying resins, are used as pressure sensitive adhesives and specifically, drug delivery patches. Said compositions can be synthesised with less difficulty compared to urethane analogues and are compatible with a wide array of different drugs.

7 Claims, 2 Drawing Sheets

(51) Int. Cl.
  *A61K 31/192*   (2006.01)
  *A61K 31/465*   (2006.01)

(56) References Cited

U.S. PATENT DOCUMENTS

2008/0045671 A1   2/2008   Scheim et al.
2015/0166858 A1   6/2015   Goubard
2020/0405909 A1*  12/2020  Taton ................. C08G 18/3243

FOREIGN PATENT DOCUMENTS

| EP | 2231740 | | 9/2010 | | |
|---|---|---|---|---|---|
| KR | 19990008023 | A | 1/1999 | | |
| WO | 1996034028 | A1 | 10/1996 | | |
| WO | 2008060506 | A2 | 5/2008 | | |
| WO | 2009085285 | A1 | 7/2009 | | |
| WO | 2017077284 | | 5/2017 | | |
| WO | WO-2017077284 | A1 * | 5/2017 | ............. | A61K 31/00 |

OTHER PUBLICATIONS

International Search Report and Written Opinion dated Dec. 18, 2019 in PCT International Application No. PCT/GB2019/052003.
International Preliminary Report on Patentability dated Feb. 11, 2020 in PCT International Application No. PCT/GB2019/052003.
JPO; English translation of Notification of Reasons for Rejection dated Jun. 26, 2023 in corresponding Japanese Appl. No. 2021-503055.
Korean Intellectual Property Office, Request for the Submission of an Opinion in Application No. 10-2021-7004898 dated Mar. 18, 2024.

* cited by examiner

PATCH

CROSS REFERENCE TO RELATED APPLICATIONS

This application is a U.S. national stage entry under 35 U.S.C. § 371 of International Application No. PCT/GB2019/052003 filed Jul. 18, 2019 entitled "PATCH," which claims priority to, and the benefit of, Great Britain Patent Application Serial No. 1811834.9, filed on Jul. 19, 2018. Each of the foregoing applications are hereby incorporated by reference in their entirety (except for any subject matter disclaimers or disavowals, and except to the extent of any conflict with the disclosure of the present application, in which case the disclosure of the present application shall control).

FIELD OF INVENTION

The invention relates to compositions for use as adhesives and for use in transdermal drug delivery (specifically patches) in combination with one or more drugs intended for transdermal drug delivery, and the processes used to make said compositions.

BACKGROUND TO THE INVENTION

Transdermal drug delivery is a known method of administering drugs to a patient. This method is typically considered distinct from injection as drugs are allowed to permeate through the skin barrier based on their solubility and size rather than being assisted through the dermis with penetrative means.

Transdermal drug delivery is often a preferred means of providing drugs to a patient as many patients do not like more invasive procedures such as injection. Therefore, patient compliance and preference is typically higher for patch technologies. However, there are problems with such technologies.

One of the problems associated with drug delivery patches is that they are frequently unable to adequately store and convey the desired active agents onto, into and/or through the skin. This problem is not as commonly observed with alternative transdermal delivery systems, such as gel compositions. However, gel compositions are often messy to use and/or do not promote gradual diffusion of active agents. The drugs contained within the gels are imparted to the skin quickly and so do not provide a prolonged therapeutic effect. It is also difficult to control the dosage of drugs when using gels.

Accordingly, it is desirable to provide a system, preferably a patch system, which is capable of not only storing and transmitting active compounds to the skin but that does so with a suitable diffusion profile over time so as to ensure maximum effectiveness of the delivered compounds during a certain time period. The system should ideally have good adhesion to the skin to keep the system in place but be easily removable causing little discomfort and leaving no residues.

WO2017077284 describes a transdermal drug delivery patch with excellent properties that overcomes the above issues. However, there are drawbacks to this system.

Firstly, the reaction between the polyols and diisocyanates described in WO2017077284 is a relatively slow process and this necessitates the use of catalysts which, even in small quantities, can be undesirable in certain commercial products and downstream applications.

Secondly, the temperatures necessary to achieve acceptable rates of reaction for both polymerisation and curing of such polymers (even in the presence of a catalyst) are frequently high which increases the cost of large scale industrial manufacture and potential for thermal reaction and/or degradation of the drug and excipients.

Therefore, it is desirable to find a polymer composition which provides these advantages, ideally without sacrificing the primary properties of such polymer, such as adhesion, or rendering such compositions incompatible with downstream applications such as drug delivery (e.g. by reducing drug load capacity and the like).

The invention is intended to overcome or at least ameliorate these issues.

SUMMARY OF THE INVENTION

There is provided in a first aspect of the invention, a composition for use as a pressure sensitive adhesive, the composition comprising: a silyl-containing polymer obtainable by polymerising: a first difunctional compound; and a second difunctional compound; wherein the first and second difunctional compounds together comprise a terminal amine group and a terminal isocyanate group; and wherein the composition further comprises a tackifying resin.

The inventors of the present invention have found that incorporating urea linkages into the polymer backbone of cross-linked silyl-containing polymers results in an improvement in the speed of the polymerisation process, allows lower temperatures to be utilised and in many cases avoids the need for a catalyst.

Accordingly, it is typically the case that the first and second difunctional compounds are polymerised in the absence of a polymerisation catalyst. As the skilled person will be aware, whilst catalysts are often present in small amount, residual amounts of catalyst in a reaction mixture can be problematic. This is often true in polymer reactions as the resulting polymers can sometimes entrap material making it hard to filter out residue catalyst. Moreover, even though only small amounts of catalyst are typically required to produce a satisfactory increase in rate of many polymerisation reactions, the presence of residue catalysts and/or compounds derived from the catalyst (even in very small quantities) can render polymers containing residual catalyst unsuitable for certain commercial applications (especially in the fields of pharmaceuticals and medical devices).

Whilst there is no particular restriction on the choice of polymerisation catalysts, typical catalysts may comprise substances such as tin (which may include elemental tin and tin in different oxidation states) or 1,4-diazabicyclo[2.2.2]octane (DABCO). Of those catalysts available, tin is commonly used in prior art processes as it is an effective catalyst for many polymerisation reactions and is relatively inexpensive. The present invention does not need a catalyst which simplifies the process.

Cross-linking the silyl-containing polymers described herein allows the polymers to form a network of covalently interconnected macromolecules which enhance properties relating to both adhesion and also drug delivery. The silyl groups of adjacent molecules interact with one another under the right conditions in the presence of moisture forming covalent linkages between molecules. A catalyst is typically used during cross-linking, though there is no particular restriction on the choice of catalyst.

The term "difunctional" as used herein is intended to refer to the presence of two functional groups typically located at each terminal end of a compound. However, said groups could be located at other points throughout the compound providing this does not prevent propagation. As the skilled person would be aware, amines react with isocyanates to form urea linkages. Typically, one of the compounds used to make the polymer has an isocyanate group and the other has an amine group. Each of the two functional groups on the first or second difunctional compounds need not be an amine or isocyanate. Other groups may be present in combination with the amine or isocyanate. Moreover, the term "difunctional" is not intended to be construed as meaning only two groups. Additional groups may be provided.

The terms "alkyl", "heteroalkyl", "cycloalkyl", "alkenyl", "heteroalkenyl", "aryl" and "heteroaryl" as used herein are intended to carry their typically meaning in the art. However, provided no adverse interactions occur that might hinder either polymerisation or curing of the polymers described herein, it is envisaged that one or more hydrogen atoms may be displaced with halogens, such as fluoride.

Whilst it may be the case that only one compound is used that comprises both an amine and an isocyanate group, it is typical that the compound bearing the isocyanate group is different to the compound bearing the amine group and hence the first and second compounds may alternately comprise an amine group and an isocyanate group.

It is often the case that one of the first or second difunctional compounds is polymeric and the other is monomeric. The polymeric compound can be modified and functionalised to suit the characteristics of particular drugs or a required dosage regimen. This may include adding additional functionality into the structure (for instance, so as to enhance hydrophilicity or increase rigidity) or changing the molecular weight of the polymeric compound to further modify the physical characteristics. It is typically the case that the polymeric compound has a molecular weight in the range of about 500 daltons to about 10,000 daltons, more typically about 1000 daltons to about 8000 daltons, more typically still about 1500 daltons to about 6000 daltons and most typically about 2000 to about 4000 daltons. Most typically, this polymeric group will be a polyether, polyester, polythioether, polycarbonate, or combinations thereof. Often, it will be a polyether such as polyethylene glycol or polypropylene glycol.

It is usually the case that the first or second difunctional compound comprising the amine is polymeric and it is also therefore often the case that the first or second compound comprising the isocyanate group is monomeric.

Whilst each of the difunctional compound bearing the amine group and the difunctional compound bearing the isocyanate group may comprise a different group to facilitate propagation of the polymer (i.e. a non-amine group and a non-isocyanate group respectively), it is typically the case that the difunctional compound bearing the isocyanate group is a diisocyanate i.e. both propagating groups are an isocyanate. One of the two functional groups may be an electrophilic species similar to an isocyanate but this is less common than the use of a diisocyanate. Further, the difunctional compound bearing the amine group may comprise an amine and another nucleophilic group capable of attacking an isocyanate to ensure propagation of the polymer. Typical nucleophilic groups include, but are not limited to: alcohols, thiols, amides or carboxylic acids. Of these, alcohols and thiols are typically the most common non-amine groups. However, it is typically the case that the first or second compound bearing the amine group comprises two amine groups, i.e. it is a diamine.

Typically the amine groups are a primary or secondary amine. The amine may be a secondary amine which may have a structure of —NRH, wherein R is selected from: alkyl, alkenyl, aryl, heteroalkyl, heteroalkenyl, heteroaryl and cycloalkyl. Most typically, R will be an alkyl or cycloalkyl group and more typically still a $C_1$ to $C_{10}$ alkyl group, often selected from: methyl, ethyl, propyl and butyl. Typically, R is methyl. In most situations, the amine group will be a primary amine i.e. —$NH_2$.

It is often the case that the first and second difunctional compounds are alternatively a diamine and a diisocyanate. This maximises the number of urea functionalities with the polymer structure.

It is typically the case that the first and second difunctional compounds have structures according to Formulae I and II respectively or Formulae Ia and IIa respectively and the silyl-containing polymer is obtained by polymerising either the first and second difunctional compounds have structures according to Formulae I and II or by polymerising those of Formulae Ia and IIa:

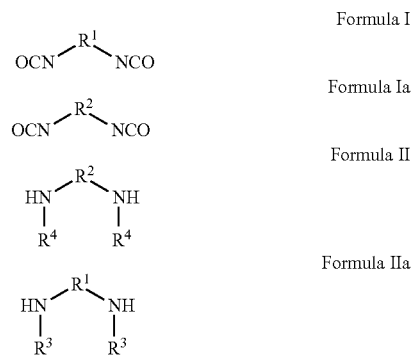

wherein
$R^1$ is selected from alkyl, alkenyl, aryl, heteroalkyl, heteroalkenyl, heteroaryl and cycloalkyl;
$R^2$ is selected from: polyethers, polyesters, polythioethers, polycarbonates, or combinations thereof;
$R^3$ and $R^4$ are each independently selected from: H, alkyl, alkenyl, aryl, heteroalkyl, heteroalkenyl, heteroaryl and cycloalkyl.

Usually, $R^1$ is an alkyl, heteroalkyl or cycloalkyl. Provided the structure of $R^1$ is capable of supporting two isocyanate groups and does not contain species which would intramolecularly react with one or both of the isocyanate groups, there is no particular restriction upon the alkyl, heteroalkyl or cycloalkyl from which $R^1$ may be chosen.

As regards $R^2$, the particular choice of $R^2$ may be selected based on the drug for delivery. However, where $R^2$ is a polyalkylether, excellent properties have been observed by the inventors. There is no particular limitation on the choice of polyalkylether but it is typically the case that a $C_1$-$C_{10}$ polyalkylene glycol is used and, of these polyethylene glycol, polypropylene glycol and polybutylene glycol are preferred. Most typically, polypropylene glycol is used. Whilst $R^2$ may be a polyether, polyester, polythioether, polycarbonate, or combinations thereof, this does not mean that additional monomers may not be incorporated into said polymers. For example, non-ether linkages may be introduced into a polyether and ether linkages may be introduced into a polythioether. The polymers may be copolymers (e.g. combinations of polyether and polyester) and arranged in a block, random or alternating configuration. Therefore, reference to a particular such polymer is intended to be understood as describing the majority of its properties and structure. However, pure forms of said polymers (e.g. a polyether consisting exclusively of polyether linkages) are also envisaged.

Each of $R^3$ and $R^4$ are usually small species such as a H or a $C_1$ to $C_{10}$ alkyl group. Often, $R^3$ and $R^4$ are selected from: H, methyl, ethyl, propyl and butyl. Typically, $R^3$ and $R^4$ are independently H or methyl. Small species, such as H or methyl, do not sterically hindering the polymerisation reaction. Most typically, $R^3$ and $R^4$ will both be H.

The invention is intended to encompass not just compositions comprising silyl-containing polymers which are obtainable from the polymerisation of the first and second difunctional compounds described herein, but also situations where additional compounds are introduced into the structure of the polymer.

Compounds additional to the first and second difunctional compounds described herein may be incorporated into the silyl-containing polymer. Said further compounds may be difunctional compounds comprising amine or isocyanate groups but which are different to the first and second compounds. Said further compounds may also comprise entirely different groups to the first and second compounds, though they will typically also be difunctional. Said further compounds may be introduced during or after polymerisation of the first and second compounds depending upon whether an alternating, random or block copolymer arrangement is desired. However, typically, the silyl-containing polymer is obtained without such further compounds.

Often, the ratio of the first and second difunctional compounds is in the range about 1:2 to about 2:1, more typically about 3:2 to about 2:3 and most typically about 1:1. In some embodiments it is desirable to have an approximately equal mixture of each of the first and second compounds as those often encourages high molecule weights. However, an excess of one of these two compounds may be desirable to reduce the molecular weight and to ensure the identity of the terminal end groups allowing an optimal selection of a silyl containing capping ligand. Accordingly, in some embodiments, one of the first and second difunctional compounds may be present in an excess in the range of about 200% to about 25%, more typically about 150% to about 50%, more typically still about 80% to about 120%, and most often approximately 100%.

As mentioned above, the silyl-containing polymer is obtainable by polymerising the first and second difunctional compounds. The silyl-containing group may already be provided as part of the first or second difunctional compounds but typically it is the case that the silyl group or groups are provided at terminal ends of the silyl-containing polymer. As such, it is often the case that "capping ligands" are used once the polymerisation of the first and second difunctional compounds has been completed so as to introduce the one or more silyl groups onto the terminal ends of the silyl-containing polymer.

It is often the case that two silyl groups are provided and typically these are at each end of the polymer chain. It is typically the case that the polymers have two or more silyl groups. Whilst only one silyl group is required for cross-linking to occur between adjacent polymer chains, it has been found that having two or more improves the degree of cross-linking that can occur. The amount of cross-linking can be varied by increasing the number of silyl groups thus allowing the skilled person to tailor the required level of cross-linking to suit a particular application (e.g. based on dosage of drug to be carried, the duration over which the drug is required to be released and the particular type of drug being carried, etc).

In one embodiment of the invention, the first and second difunctional compounds have structures according to Formula III and IV respectively or Formula IIIa and IVa respectively:

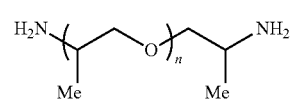

Formula III

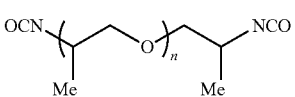

Formula IIIa

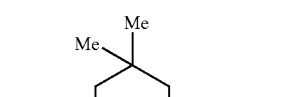

Formula IV

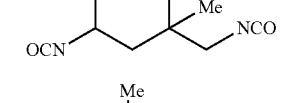

Formula IVa wherein
"n" is an integer in the range of about 20 to about 200, typically about 30 to about 140 and more typically about 40 to about 80. In an alternative embodiment, each of the methyl groups present in each of formulae III and IIIa may be independently replaced with hydrogen.

The silyl group used in the present invention is not especially limited and can be attached to the polymer via a linker that will typically contain a $C_1$-$C_{10}$ alkyl or heteroalkyl chain and the silyl group may typically comprises three $C_1$-$C_{10}$ alkyl and/or alkoxy species. A typical terminal silyl group that may be reacted with the above described polymer to obtain the silyl-containing polymer are shown in Formulae V and Va:

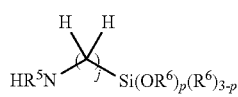

Formula V

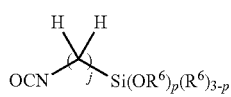

Formula Va wherein
"p" is an integer between 3 and 0;
$R^5$ is independently selected from: H, alkyl, alkenyl, aryl, heteroalkyl, heteroalkenyl, heteroaryl and cycloalkyl;
$R^6$ is $C_1$-$C_{10}$ alkyl; and
"j" is an integer between 1 and 10.

As the person skilled in the art will appreciate, the choice of compound used to introduce the silyl group into the polymer is determined to a large extent by the ratio of the first and second difunctional compounds used in the polymerisation reaction (as this determines the terminal end groups available to react with these so called "capping"

ligands). However, the final structure is essentially the same. Typically however, "j" is in the range of 2 to 5 and more typically 3 or 4. Further, "p" is usually 3 and $R^6$ may be independently selected from methyl, ethyl, propyl or butyl, most typically $R^6$ is methyl or ethyl.

The general structure of the silyl-containing polymer may typically be that according to Formulae VI and/or VIa:

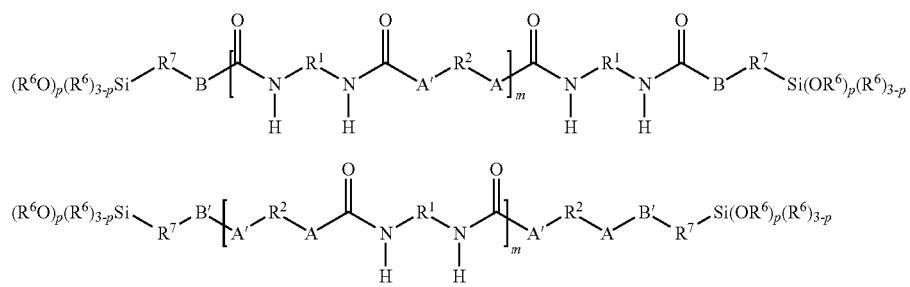

Formula VI

Formula VIa wherein
"p" is an integer in the range 3 to 0;
"m" is an integer in the range about 1 to about 200;
A' and A are each independently selected from: $-NR^4-$, $-NR^3-$, $-O-$ or $-S-$ with the proviso that at least one of A' or A is $-NR^4-$, $-NR^3-$;
B is a nucleophilic species;
B' is an electrophilic species;
$R^6$ and $R^7$ are each independently a $C_1$-$C_{10}$ alkyl or heteroalkyl; and
$R^1$, $R^2$, $R^3$ and $R^4$ are as described above.

It is typically the case that each of A' and A are both $-NR^4-$ and moreover that $R^4$ may be selected from: H or a $C_1$ to $C_5$ alkyl or heteroalkyl. However, most typically $R^4$ is hydrogen. Moreover, B is typically selected from $-NR^5-$, $-O-$ or $-S-$ as each of these can be formed easily by reacting the terminal isocyanate with a silyl capping ligand comprising: $-NR^5H$, $-OH$ or $-SH$ respectively (wherein $R^5$ is as described above). Typically, B is $-NR^5-$ and most typically $-NH-$. As regards B', this species is typically any group capable of reacting with nucleophile A' and is most commonly an isocyanate derivative i.e. B' may be $-C(O)$ NH—. Each of B and B' is intended to allow the silyl capping ligand to affix itself to the terminal end of the polymerised diamine diisocyanate.

The precise length of the capping silyl group (and hence the identity of $R^7$) is not particularly limited within the range of $R^7$ being $C_1$-$C_{10}$ alkyl or heteroalkyl. $R^7$ merely functions as a spacer between the functional group capable of attaching the capping ligand to the main polymer the silyl group itself. However, it is typically the case that $R^7$ is $C_2$ to $C_8$ alkyl or heteroalkyl, more typically $C_3$ to $C_5$ alkyl or heteroalkyl and most typically a $C_3$ alkyl or heteroalkyl. Typically $R^7$ is an alkyl group.

Usually, "p" an integer of either 3, 2 or 1; more typically 2 or 3; and most typically 3. In addition, $R^6$ is often a $C_1$-$C_4$ alkyl or heteroalkyl. More typically, $R^6$ is an alkyl group and more typically still $R^6$ is methyl or ethyl. Most typically, $R^6$ is methyl or ethyl.

There is no particular restriction on the value of "m" with the range about 1 to about 200. However, typically "m" is an integer in the range about 10 to about 150; more typically in the range about 15 to about 120; more typically still in the range about 20 to about 80; and even more typically still in the range about 25 to about 50. The precise molecular weight of the silyl-containing polymer may be varied by changing the value of "m" to suit a particular application.

As explained above, additional compounds may be worked into this structure to produce a variety of copolymers. For instance, this may produce structures according to general formula VIIa:

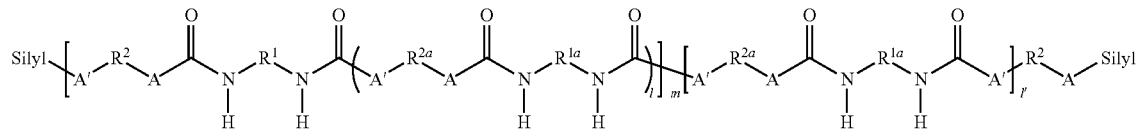

Formula VIIa wherein
A', A, $R^1$, $R^2$ and "m" are as described above;
I and I' are each an integer independently selected 0 to 200;
$R^{1a}$ and $R^{2a}$ are each independently selected from: alkyl, alkenyl, aryl, heteroalkyl, heteroalkenyl, heteroaryl and cycloalkyl; polyethers, polyesters, polythioethers, polycarbonates, or combinations thereof.

This structure is analogous to formula VIa wherein further compounds have been introduced and the terminal silyl groups described in VIa have been abbreviated using the term "silyl". A corresponding structure based on formula VI is also envisaged (wherein an excess of isocyanate is employed).

Typically, one or both of I and I' is 0. In some embodiments, I is 1. It may be the case that I' is equal to "m". Moreover, $R^2$ may be equal to $R^{2a}$ and/or $R^1$ may be equal to $R^{1a}$. In some instances, I and I' may each be an integer independently selected from 1 to about 180; typically about 20 to about 180; more typically about 40 to about 160; more typically still about 60 to about 140; even more typically about 80 to about 120; and even more typically still about 90 to about 110. Often, one or both of I and I' may be an integer independently selected from 1 to about 60, more typically 1 to about 40 and even more typically, 1 to about 20.

In one embodiment of the invention, the silyl-containing polymer may be capped with a silyl group at one terminal and the other terminal may be bonded to a multi-valent linker species. The term "multi-valent linker" is intended to encompass molecules which have two more groups that are capable of reacting with other species thereby effectively forming a molecular hub to which two or more compounds can be attached. In the present case, two or more of the polymers obtained by the polymerisation of the first and second difunctional compounds can be attached to the multi-valent linker and subsequently capped at the one remaining terminal with a silyl group. This is represented in Formulae VIII and VIIIa:

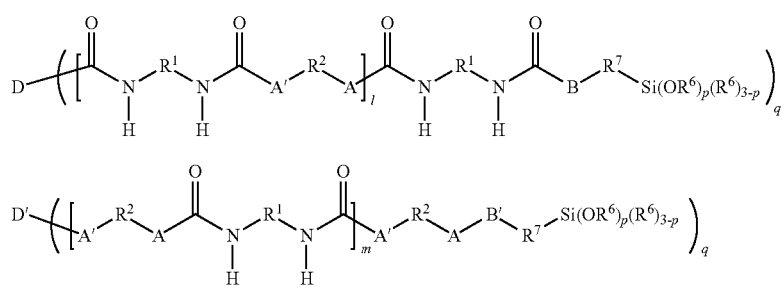

Formula VIII

Formula VIIIa wherein

A', A, B, B', $R^1$, $R^2$, $R^6$, $R^7$, "m" and "p" are as described above;

q is an integer in the range of 2 to 4; typically 3 or 4; more typically 2 or 3; more typically still 3; even more typically 2; and in some circumstances 4;

D is a multi-valent linker comprising in the range of 2 to 4 nucleophilic groups; and D' is a multi-valent linker comprising in the range of 2 to 4 electrophilic groups.

D typically comprises 2 to 4 groups independently selected from —$NR^5$—, —O— or —S— forming bonds with the main polymer by reacting the terminal isocyanate group (in this case) with —$NR^5$H, —OH or —SH respectively. Typically, D comprises 2 to 4 —$NR^5$— groups (wherein $R^5$ is as described above) and more typically —NH— groups. As regards D', this multi-valent linker typically comprises 2 to 4 electrophilic groups capable of reacting with nucleophile A' and said electrophilic group is most commonly an isocyanate derivative i.e. D' may comprise-C(O) NH— groups. Each of D and D' may typically comprise 3 or 4 nucleophilic or electrophilic groups respectively, more typically 2 or 3 and most typically 3. However, configurations with 2 groups and configurations with 4 groups are also envisaged.

There is provided in an alternative embodiment of the invention, a composition for use as a pressure sensitive adhesive, the composition comprising a cross-linked silyl-containing polymer, wherein said polymer has a structure according to Formula IX:

Formula IX

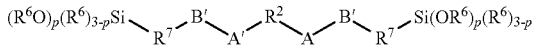

wherein

A', A, B', $R^2$, $R^6$, $R^7$ and "p" are as described above; and wherein the composition further comprises a tackifying resin.

The inventors have found that, in addition to the copolymer described in the first aspect of the invention, cross-linked polymers having a structure according to formula IX (comprising a single difunctional polymeric compound functionalised with two silyl-groups) can in combination with a tackifying resin also function well as pressure sensitive adhesives, despite the absence of a plurality of urea linkages. This is advantageous as the polymerisation process requires fewer steps.

As described above in relation to the first embodiment of the invention, one or more additional monomers may be incorporated into the polymer structure. Moreover, situations are also envisaged where a multivalent molecule is functionalised to accommodate multiple polymers similar to that described in formulae VIII and VIIIa above. Accordingly, the polymer may have a structure according to formula X:

Formula X

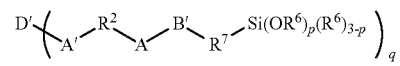

wherein D', A', A, B', $R^2$, $R^6$, $R^7$, "p" and "q" are as described above.

As explained above A', A, B', $R^2$, $R^6$, $R^7$ and "p" are as described above and a typical structure for the above compound is shown below in formula XI:

Formula XI

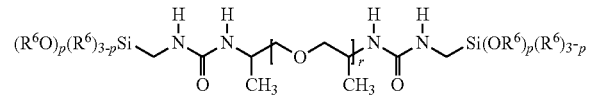

In an alternative embodiment, each of the methyl groups ($CH_3$) present in formula XI may be independently replaced with hydrogen.

With respect to either of the embodiments described above, it is also typically the case that the polymers further comprises a least one group adapted to dissolve or disperse the at least one drug for drug delivery to the skin. The polymers may be functionalised to contain a variety of functional groups in order to imbue the polymer with various properties e.g. to improve the characteristics of drug delivery. In particular, monomer units or pendent moieties may be incorporated into the polymer which improve the solubility or dispersability of a given drug to be delivered. Depending on the drug to be delivered and the drug delivery profile required, a range of monomer units and functional groups can be introduced to provide the desired characteristics. For instance, the polymer may include moieties of polyethylene glycol within its structure in order to increase hydrophilicity.

Compositions according to the invention have been found to function well as adhesives, and in particular as adhesive tapes. Moreover, in one embodiment of the invention, the compositions may carry ingredients for delivery to a user's skin.

In one preferred embodiment the compositions of the invention may further comprise one or more drugs and be used to deliver drugs "to the skin". By, "to the skin" it is meant that the drugs are administered either: onto the surface of the skin; into the skin; or delivered to the body transdermally i.e. through the skin and into the blood stream.

The term "drug" as used herein is intended to refer to a biologically active substance. There is no particular limitation on the type of compound from which the drug is made. The drugs used with the present invention are typically molecules with low molecular weight, especially where the drug is intended for transdermal delivery. However larger molecules and macromolecules are also envisaged including biological compounds such as peptides and proteins. The term "drug" is also intended to encompass pharmaceutically acceptable salts of biologically active substances. It is also envisaged that the drug may provide a physical effect on the body, such as heating or cooling, which may have a therapeutic effect.

The term, "small molecule drugs" is intended to encompass those compounds typically produced by synthetic chemical processes having a molecular weight typically less than 1000 Da, more typically less than 700 Da.

The term "polymer" is intended to refer to macromolecules comprised of a plurality of repeating monomer units, typically having a weight average molecular weight of greater than 600 Da, preferably greater than 2000 Da.

The term "cross-linked" as used herein is intended to refer to the covalent interconnection of polymers within compositions either directly (polymer to polymer) or indirectly (polymer to intermediate bridging group to polymer) typically as a result of a reaction between particular polymer side groups and other corresponding side groups on adjacent polymers or intermediate bridging groups. This may be achieved using a catalyst and/or with the presence of co-reactants, such as water. Further, elevated temperatures, radiation such as ultraviolet (UV) radiation or electron-beam (EB) radiation may be used to promote the cross-linking reaction. Where a catalyst is used, at least one catalyst is typically present in the composition in an amount in the range 0.001 to 5% by weight, more typically 0.01 to 3% by weight of the composition. The catalyst may remain in the composition or may be used up in the cross-linking process.

The term "curing" as used herein is to be understood as "cross-linking" (as described above) the components of a composition together until the desired properties of the cured material are achieved. This cross-linking in the present invention typically occurs between silyl groups of adjacent silyl-containing polymers of the kind described above.

It is typically the case that the silyl-containing polymers described above will have a weight average molecular weight in the range 700 Da to 250 kDa, more typically from 6 kDa to 100 kDa and even more typically from 8 kDa to 50 kDa.

The dispersity of the silyl-containing polymers is typically less than 3, more typically less than 2 and is most typically in the range 1.0 to 1.6, typically 1.1 to 1.4.

The compositions of the invention include a compatible tackifying resin. This improves the adhesive properties of the composition and allows the composition to be formulated into a pressure sensitive adhesive (PSA). Compositions including a compatible tackifying resin provide good adhesion to the skin and can be removed effectively leaving negligible residue. Without being bound by theory, it is speculated that a synergistic interaction between the silyl-containing polymers described above and the tackifying resin occurs which minimises the reduction in adhesive qualities when compounds are solubilised in the material. Accordingly, the invention also encompasses pressure sensitive adhesives comprising the composition described above.

The ratio of tackifying resin to silyl-containing polymer is typically in the range 1:10 to 10:1, more typically, 1:2 to 2:1 and is typically about 1:1. The composition typically comprises: a) from 20 to 85% by weight, or more typically 30 to 60% by weight of the at least one silyl-containing polymer described above; and b) from 15 to 80% by weight, or more typically 30 to 60% by weight of at least one tackifying resin. Typically the composition comprises about 50% silyl-containing polymer and about 50% tackifying resin.

The tackifying resin may be selected from: phenol modified terpene resins (typically polyterpenes), hydrocarbon resins (typically where the hydrocarbons have an aromatic character, i.e. comprise one or more aromatic groups), rosin ester resins, modified rosin ester resins and acrylic resins. Typically, the phenol modified terpene resins have a softening point from, 70° C. to 150° C., or more typically 110° C. to 130° C.; the hydrocarbon resins have a softening point in the range 10° C. to 150° C. and more typically 70° C. to 120° C.; and the rosin ester resins have a softening point in the range 10° C. to 130° C., more typically 90° C. to 110° C.

The softening point of the silyl-containing polymer and/or of the tackifying resin can be measured according to ASTM E28 standard.

The tackifying resins are typically compatible with the skin and do not cause irritation, and are substantially non-cytotoxic. Further, the tackifying resins are typically resistant to degradation. Where the tackifying resins do break down over time (e.g. due to photolysis or hydrolysis during use or storage) it is typically the case that the breakdown products are substantially non-toxic and typically do not penetrate the skin.

Typically, the phenol modified terpene resins are obtained by polymerization of terpene hydrocarbons and phenols, in the presence of Friedel-Crafts catalysts.

According to one embodiment, hydrocarbon resins are selected from: resins obtained by a process comprising the polymerization or co-polymerization of [alpha]-methyl-styrene, said process possibly also including a reaction with phenols, resins obtained by hydrogenation, polymerization or co-polymerization (with an aromatic hydrocarbon) of mixtures of unsaturated aliphatic hydrocarbons having less than or equal to 10 carbon atoms derived from petroleum fractions, optionally grafted with maleic anhydride, terpene resins, generally resulting from the polymerization of terpene hydrocarbons such as, for example, monoterpene (or pinene) in the presence of Friedel-Crafts catalysts, copolymers based on natural terpenes, for example styrene/terpene, [alpha]-methylstyrene/terpene and vinyltoluene/terpene.

According to one embodiment, rosin ester resins are selected from natural or modified rosins, such as for example the rosin extracted from pine gum, wood rosin extracted from tree roots and their derivatives that are hydrogenated, dimerized, polymerized or esterified by monoalcohols or polyols such as glycerol.

According to one embodiment, the molecular weight of the non-acrylic resins as above-disclosed is less than or equal to 10,000 Da, typically less than or equal to 2000 Da, more typically less than or equal to 1000 Da.

An acrylic resin is defined as a polymer or oligomer built with a significant amount of (meth)acrylic and/or (meth) acrylate monomers, usually at least 5% weight/weight (w/w), more often at least 10% w/w, still more usually at least 20% w/w, typically at least 30% w/w in the polymeric chain.

According to one embodiment (meth)acrylic monomers are chosen from acrylic acid, methacrylic acid, methyl acrylate, methyl methacrylate, ethyl acrylate, ethyl methacrylate, butyl acrylate, butyl methacrylate, isobutyl acrylate, isobutyl methacrylate, n-hexyl acrylate, n-hexyl methacrylate, 2-ethylhexyl acrylate, ethylhexyl methacrylate, n-heptyl acrylate, n-heptyl methacrylate, stearyl acrylate, stearylmethacrylate, glycidyl methacrylate, alkyl crotonates, vinyl acetate, di-n-butyl maleate, di-octylmaleate, acetoacetoxyethyl methacrylate, acetoacetoxyethyl acrylate, acetoacetoxypropyl methacrylate, acetoacetoxypropyl acrylate, diacetone acrylamide, acrylamide, methacrylamide, hydroxyethyl methacrylate, hydroxyethyl acrylate, allyl methacrylate, tetrahydrofurfuryl methacrylate, tetrahydrofurfuryl acrylate, cyclohexylmethacrylate, cyclohexyl acrylate, n-hexyl acrylate, n-hexyl methacrylate, 2-ethoxyethyl acrylate, 2-ethoxyethyl methacrylate, isodecyl methacrylate, isodecyl acrylate, 2-methoxy acrylate, 2-methoxy methacrylate, 2-(2-ethoxyethoxy) ethylacrylate, 2-phenoxyethyl acrylate, 2-phenoxyethyl methacrylate, isobornyl acrylate, isobornyl methacrylate, caprolactone acrylate, caprolactone methacrylate, polypropyleneglycol monoacrylate, polypropyleneglycol monomethacrylate, polyethylenegly col (400) acrylate, polypropyleneglycol (400) methacrylate, benzyl acrylate, benzylmethacrylate, N-vinyl pyrrolidone or N-vinyl lactam.

Typically, (meth)acrylic monomers have up to 20 carbon atoms, and are typically selected from acrylic acid, methacrylic acid, butyl acrylate, 2-ethylhexyl acrylate and hydroxyethylacrylate.

According to one embodiment, acrylic resins are selected from polymers containing at least one (meth)acrylic function or chain part and at least one hydrocarbon chain part, said polymers can be in the form of copolymers, grafted or reacted or block polymers.

The above described resins have a viscosity measured at 100° C. significantly greater or equal to 100 Pa·s, and less than or equal to 100 Pa·s at 150° C. The acrylate resins may comprise repeating units of at least one hydrocarbon monomer and at least one acrylate monomer. Hydrocarbon monomers are selected from the group consisting of styrene, alpha-methyl styrene, vinyl toluene, indene, methylindene, divinylbenzene, dicyclopentadiene, and methyl-dicyclopentadiene, and polymerizable monomers contained in $C_5$-pyperylenic and $C_5$-isoprene and $C_9$-aromatic available streams from the petrochemical industry. Those hydrocarbon monomers are usually polymerized together in various ratios by cationic polymerization using Lewis acid catalysts. Acrylate monomers have the general formula $R_a$—CH=$CR_b$—$COOR_c$ wherein $R_a$, $R_b$, $R_c$ are independently selected from hydrogen, aliphatic groups, and aromatic groups. Acrylate monomers are selected from the group consisting of methyl acrylate, acrylic acid, methacrylic acid, methylmethacrylate, ethyl acrylate, ethylmethacrylate, butyl acrylate, butylmethacrylate, isobutyl acrylate, isobutylmethacrylate, n-hexyl acrylate, n-hexylmethacrylate, ethylhexyl acrylate, ethylhexyl methacrylate, n-heptyl acrylate, n-heptyl methacrylate, 2-methyl heptyl(meth)acrylate, octyl acrylate, octyl methacrylate, isooctyl (meth)acrylate, n-nonyl(meth)acrylate, iso-nonyl(meth)acrylate, decyl (meth)acrylate, isodecyl acrylate, isodecyl methacrylate, dodecyl (meth)acrylate, isobornyl (meth)acrylate, lauryl methacrylate, lauryl acrylate, tridecyl acrylate, tridecyl methacrylate, stearyl acrylate, stearylmethacrylate, glycidylmethacrylate, alkyl crotonates, vinyl acetate, di-n-butylmaleate, di-octylmaleate, acetoacetoxyethyl methacrylate, acetoacetoxyethyl acrylate, acetoacetoxypropyl methacrylate, acetoacetoxypropyl acrylate, diacetone acrylamide, acrylamide, methacrylamide, hydroxy ethylmethacrylate, hydroxyethyl acrylate, allyl methacrylate, tetrahydrofurfuryl methacrylate, tetrahydrofurfuryl acrylate, cyclohexyl methacrylate, cyclohexyl acrylate, n-hexyl acrylate, n-hexyl methacrylate, 2-ethoxyethyl acrylate, 2-ethoxyethyl methacrylate, isodecyl methacrylate, isodecyl acrylate, 2-methoxy acrylate, 2-methoxy methacrylate, 2-(2-ethoxyethoxy)ethylacrylate, 2-phenoxyethyl acrylate, 2-phenoxyethyl methacrylate, isobornyl acrylate, isobornyl methacrylate, caprolactone acrylate, caprolactone methacrylate, polypropyleneglycol monoacrylate, polypropyleneglycol monomethacrylate, poyethyleneglycol (400) acrylate, polypropyleneglycol (400) methacrylate, benzyl acrylate, benzylmethacrylate, sodium 1-allyloxy-2-hydroylpropyl sulfonate, acrylonitrile, and mixtures thereof.

Typically, hydrocarbon monomers are selected among the group of aromatic monomers or polymerizable monomers from the $C_9$-aromatic stream from petrochemical sources; of dicyclopentadiene or polymerizable monomers from the $C_5$-pyperylene or $C_5$-isoprene stream from petrochemical sources.

Usually acrylate monomers are acrylic acid and 2-ethylhexyl acrylate, hydroxyethylacrylate, methacrylic acid, butyl acrylate. Softening point of such resins are typically from room temperature up to 180° C., molecular weights range in weight average is typically from 200 to 25,000 Daltons, and acid number typically ranging from 0 to 300 mg KOH $g^{-1}$. Typical resins would have molecular weight less than or equal to 10,000 Daltons, more usually less than or equal to 2000 Da, most typically less than or equal to 1000 Da; softening point less than or equal to 150° C., more typically less than or equal to 120° C., most typically ranging from 70 to 120° C.; acid number less than or equal to 150 mg KOH $g^{-1}$, more typically less than or equal to 100 mg KOH $g^{-1}$, most typically from 10 to 100 mg KOH $g^{-1}$.

According to one embodiment, the molecular weight of an acrylic resin is less than or equal to 300,000 when only one resin is present in the composition, usually less than or equal to 100,000, most typically less than or equal to 20,000.

A non-acrylic resin can still contain some acrylic functions in a non-significant quantity, either being part of the polymerization chemical reaction, or as grafted or functionalized groups onto monomers or onto the polymeric chains.

Examples of suitable resins include: phenol modified terpene resins such as, DERTOPHENE® H150 available from DRT company with a molecular weight $M_n$ equal to around 630 Da, DERTOPHENE® T having a molecular weight equal to around 500 Da available from the same company; hydrocarbons resins such as, NORSOLENE® WHO available from Cray Valley, which is obtained by polymerization of alpha-methylstyrene without the action of phenols, with a number-average molecular weight of 1000 Da, and a softening point of 110° C., NORSOLENE® W80 is of the same structure as NORSOLENE® WHO but with a lower molecular weight leading to a softening point of 80° C.; and rosin ester resins such as, SYLVALITE® RE 100 which is a pentaerythritol rosin ester available from Arizona Chemical and having a molecular weight Mn of around 1700 Da; and acrylic resins such as, KOLON® PX95 (available from Kolon Industries Inc.) or Eastman® resin described in U.S. Pat. No. 7,332,540 (formulation 1, table 3 column 14), which are polymers containing at least one (meth)acrylic function or chain part and at least one hydrocarbon chain part, said polymers can be in the form of copolymers, grafted or reacted or block polymers, Acronal® 4F available from the BASF Company, Germany, resulting from polymerization of butyl acrylate monomers.

Accordingly, the tackifying resin may be selected from: a vinylpyrrolidone-vinyl acetate copolymer, such as Kollidon VA 64; a glycerol ester of hydrogenated wood rosin, such as Foral 85; a polyisobutylene, such as Oppanol B10 or Oppanol B11; a poly(methyl methacrylate-co-butyl methacrylate-co-dimethylamino ethyl methacrylate), such as Eudragit E 100 or Eudragit E PO; a poly(ethyl acrylate-co-methyl methacrylate-co-trimethylammonioethyl methacrylate chloride), such as Eudragit RL 100 or Eudragit RS; a glycerol ester of partially dimerized rosin, such as Pexalyn Ester 10; a vinyl chloride-vinyl acetate copolymer, such as Kanevinyl MB 1008; a stabilised pentaerythritol ester of tall oil rosin, such as Sylvalite RE100; an ethenylbenzene copolymer with (1-methylethenyl)benzene, such as Cleartak W-110; a poly (vinyl pyrrolidone), such as Kollidon 90F; a sucrose acetate isobutyrate, such as Eastman SAIB-100; or a combination thereof.

The curing catalyst that may be used in the composition according to the invention may be any catalyst known to a person skilled in the art for silanol condensation. Examples of such catalysts include organic derivatives of titanium such as titanium acetyl acetonate (commercially available under the name TYZOR® AA75 from DuPont), of aluminium such as aluminium chelate (commercially available under the name K-KAT® 5218 from King Industries), of amines such as 1,8-diazobicyclo[5.4.0]undec-7-ene or DBU.

Optionally, the composition according to the invention may also include, in combination with the silyl-containing polymer, thermoplastic polymers often used in the preparation of HMPSAs, such as ethylene vinyl acetate (EVA) or styrene block copolymers.

The composition according to the invention may also comprise up to 3% of hydrolysable alkoxysilane derivatives, as a desiccant, typically a trimethoxysilane derivative. Such an agent advantageously prolongs the shelf life of the composition according to the invention during storage and transport, before the use thereof. Exemplary additives include, [gamma]-methacryloxypropyltrimethoxysilane available under the trade name SILQUEST® A-174 from US Momentive Performance Materials Inc.

The composition according to the invention may also include a plasticizer such as a phthalate like diisononylphthalate (DINP) or a benzoate, a paraffinic and naphthenic oil (such as PREVIOL® 352 from Esso) or else a wax of a polyethylene homopolymer (such as A-C® 617 from Honeywell) or a wax of a polyethylene/vinyl acetate copolymer, or else pigments, dyes or fillers.

Further, an amount of 0.1 to 3% of one or more stabilizers (or antioxidants) is typically included in the composition according to the invention. These compounds are introduced to protect the composition from degradation. These compounds may include primary antioxidants which trap free radicals and are, in particular, substituted phenols such as IRGANOX® 1076 or IRGANOX® 1010 from Ciba. The primary antioxidants may be used alone or in combination with other secondary antioxidants or UV stabilizers.

There is no particular limitation on the choice of drugs that can be used in conjunction with the composition described above providing that said drugs are soluble or dispersible in the composition. Although reference is made to "skin" throughout the application, it is contemplated that the composition could be applied to wounds and mucosal membranes (such as eyes and gums) as well. However, typically the composition is applied to the skin.

Whilst there is no particular limitation on the choice of drug, the drug will typically have a molecular weight greater than 100 Da, typically in the range 500 Da to 20,000 Da, more typically 500 Da to 10,000 Da and more typically still 500 Da to 5000 Da. Often, the range will be 100 Da to 5000 Da, more typically 100 Da to 500 Da. As explained above, low molecular weight drugs are particular desirable for transdermal drug delivery where the drug needs to penetrate the skin in order to enter the blood stream.

Often the drugs will be hydrophilic as this improves the ability of drugs to be absorbed into the blood stream (for transdermal drug delivery). Obviously, the drug must be a compound that is capable of dissolving at least partial within the cross-linked polymer matrix either alone or with the assistance of a co-solvent. Hydrophobic and amphoteric drugs are also envisaged especially for application where drugs are for application to the skin surface.

The drugs described herein are not restricted to small molecule drugs but may also encompass biological compound such as proteins, peptides, enzymes, DNA, RNA, SIRNA, antibodies or fragments thereof, vitamins, minerals or combinations thereof.

Other compounds or excipients can be added to improve the effectiveness or distribution profile of the drugs. For instance, dyes, pigments, antioxidants, desiccants, pH buffers to maintain stability of drugs for delivery or the drugs may be encapsulated within carriers such as micelles to improve their delivery further. Polymeric materials other than those described above may also be provided, for instance, in order to modify physical characteristics of the composition.

The drugs used are typically selected from the group consisting of: analgesics, antiinflammatory drugs, hormones, anti-addiction drugs such as nicotine, anti-hypotension drugs, anti-depressants, anti-Alzheimer's drugs, anti-infective, anti-scarring drugs, anti-psychotics, metabolic modulators, pigmentation, nutrients, minerals and vitamins.

It is typically the case that the drug used is an analgesic and may be selected from the group consisting of: capsaicin, isobutylphenylpropanoic acid (ibuprofen), flurbiprofen, methyl salicylate, diclofenac, diclofenac epolamine, levomenthol, salicylic acid, ketoprofen, ketamine, fenbufen, fentanyl, buprenorphine, prilocaine, lidocaine, piroxiam, sufentanil, trolamine, or combinations thereof.

Where the drug is an anti-infective drug, it is typically the case that the drug is an antiviral, antibacterial or antifungal drug and examples of typical anti-infective drugs include chlorhexidine, iodine, silver nitrate, chlorquinaldol or combinations thereof.

Alternatively, the drug used may be a hormone. There is no particular restriction on the particular hormone or combination of hormones that may be used in the present invention. However, typically the hormone is selected from: buprenorphine, clobetasone butyrate, clonidine, dexamethasone, diflucortalone valerate, estradiol, oestrogen, ethinylestradiol, gestodene, hydrocortisone, levonorgestrel, norelgestromin, norethisterone, prednisolone, teriparatide, testosterone, triamcinolone, or combinations thereof.

Other drugs which may be employed are those acting upon the central nervous system (CNS drugs) typical examples of which include: olanzapine, memantine, and donepezil.

In another embodiment of the invention, the drug used may be any anti-addiction drug such as nicotine, antiemetic drugs such as cannabinoids (e.g. dronabinal) and may also be selected from vitamins, nutrients, minerals, or combinations thereof.

Further example of drugs suitable for use in the composition of the invention include anti-cancer drugs, especially skin cancer.

Often, the drugs used in the composition of the present invention will comprise one or drugs selected from: nicotine, ibuprofen, meloxicam, olanzapine, memantine, donepezil, dronabinol, lidocaine, fentanyl, diclofenac, methyl salicylate, testosterone, luflunomide, terflunomide, apomorphine, ketamine, esketamine, amitriptyline, aripiprazole, colchicine, hydrocortisone, lamotrigine, loratadine, ketoprofen, naltrexone, ketorolac, granisetron, celecoxib, fulvestrant, indomethacin, agomelatine, escitalopram, fulvestrant, flurbiprofen, galantamine, methyl phenidate, mometasone, propafenone, clobazam, pramipexole, ropinirole, bisoprolol, levonorgestrel, ziprasidone, verapamil, meurafenib, propylthiouracil, methotrexate, pazopanib, maraviroc, lithium, lisdexamfetamine, huperazine a, calcitrol, temazolamib, bupropion, domperidone, lurasidone, tertracycline, progesterone, prilocaine, ivermectin, cannabidiol, artesunate, artemisinin, salsalate, or combinations thereof.

In an alternative embodiment of the invention, the composition of the invention may be used to delivery "non-drug" agents. The term, "non-drug" is intended to refer to compounds which although providing no direct treatment or preventative effect against a disease, nevertheless provide some benefit to a user. There may be some overlap between the "drugs" and "non-drugs" described herein depending upon circumstances. For instance, the delivery of a vitamin to alleviate a disorder associated with an acute vitamin deficiency may be considered a "drug" whereas the provision of vitamins for general well-being may be construed as a "non-drug" circumstance. There is no particular restriction on the type of non-drug agent that may be pair with the composition of the invention. However, typical examples include: nutraceuticals, cosmetics, stimulants, skin protectants, or combinations thereof. Of these, nutraceuticals and cosmetics are often used. The skilled person would understand how to improve the compatibility of the composition of the invention for a given non-drug or combination of non-drugs. Moreover, both drugs and non-drugs may be provided together.

The cosmetics that can be used in combination with the present invention are not especially limited. These may include transdermal cosmetics or traditional cosmetics for application to the skin's surface. The types of cosmetic products that may be desirably delivered to the skin may be selected from: anti-aging creams, anti-wrinkle cream, serums, oils, moisturisers, toners, and the like.

Again, certain non-drugs may overlap with the excipients provided with drug compounds. For instance, where the non-drug is a stimulant, this can augment the speed at which a drug paired with said stimulant begins acting upon the body. However, such compounds could be paired with the drug component.

It may also be desirable for the "non-drug" to be a skin protectant i.e. a compound which protects the skin from harmful exposure e.g. from chemical or ultraviolet light. Usually, the skin protectant will be a sunscreen (i.e. a compound which minimises the damage done to the skin by solar radiation).

A range of excipients and preservatives can be incorporated into the composition of the invention depending on the particular selection of drugs for use in the composition. Excipients can be introduced to modify the drug release properties of the composition or other properties of the composition such as the tackiness or colour of the composition. Some excipients may also have a biological effect on the body, such as caffeine, that synergise with other drugs in the composition to improve the overall effectiveness of the composition. The excipients can also be used to modify the physical characteristics of the composition, including providing heating or cooling effects when applied to the skin or softening the skin using moisturising substances.

For instance, that creates a cooling or warming sensation made be delivered to the skin. For instance, a volatile topical analgesic, such as menthol, could be added to the composition to generate a cooling sensation.

The composition may further include a solvent or co-solvent intended to improve the solubility of the drugs used in the composition of the invention. There is no particular restriction on the choice of solvent or co-solvent provided that it is compatible with the composition and improves solubility and/or release of drugs from the composition in use. Typically, the solvent or co-solvent is an organic solvent, typically a substantially non-hazardous organic solvent. The solvent is useful in reducing the viscosity of the polymer composition and therefore can be used to improve incorporation of drugs into the polymer matrix.

It is typically the case that the composition of the invention is in the form of a drug delivery patch. Typically, the patch is a transdermal drug delivery patch. The inventors have found that the claimed composition is capable of forming thin films with excellent drug retention and delivery profiles as well as demonstrating excellent skin adhesion and removal properties. The patches typically comprises a thin layer of the cured composition typically with a thickness of less than 10 mm and usually less than 5 mm. The patches may comprise a layer of the cured composition and at least one substrate layer onto which a layer of the composition is applied. This substrate layer is typically not adhesive on one surface so as to permit application of the patch by hand to a user's skin.

The patch of the present invention has several advantages over existing patch designs. As explained above, many patch adhesives are ineffective at dissolution of certain drugs or do not deliver a dosage over a prolonged period. Accordingly, many patches make use of a separate drug reservoir to perform this function. However, this typically requires additional layers to be incorporated into the patch structure and the drugs often still need to permeate through the adhesive layer to reach the skin. Some designs use a centrally positioned reservoir and a perimeter of adhesive to overcome this problem. However, this often leads to poor surface contact between the reservoir and the skin reducing the effectiveness of the patch and adhesion can often be ineffective. This is not a problem with the present invention as the composition can be formulated in a single layer, provides good adhesion and good drug delivery to the skin. In addition, the patches of the present invention can be made using milder conditions and so are able to accommodate a wider array of drugs.

The patch typically comprises a continuous or semi-continuous layer of the composition as described above sandwiched between two substrate layers. It is usually the case that at least one of the substrate layers is comprised of a releasable material which can be easily separated, typically by hand, from the composition layer prior to application of the patch. The two substrate layers may both be made from a releasable material. This releasable layer or a non-releasable "back liner" may also prevent the composition layer from drying out or leaking drug content when not in use and allows the composition layer to be manipulated more easily.

Typically, one of the layers may be made from a non-releasable material or "back liner" that bonds strongly to the composition layer. A further substrate layer comprising a releasable layer may also be applied to the other surface of the composition layer opposite the back liner layer. This allows the patch to form a plaster-type structure that prevents the composition layer from sticking to surfaces when not in use or a user's clothing when in use.

The substrate is adapted to carry the composition and may be a release liner, a carrier film or web. Often the releasable layer comprises a siliconised surface covering all or substantially all of the surface and/or is made from a siliconised material. The releasable layer may be any polymer film that allows release from the composition layer such as PTFE or similar materials.

There is provided in a second aspect of the invention, a process for preparing the composition according to the first aspect of the invention, comprising: a first step of providing a silyl-containing polymer and a tackifying resin according to the first aspect of the invention; a second step of dissolving a drug for delivery to the skin into the mixture; and a third step of curing the mixture.

Alternatively, the drug may be added after the third step of curing the mixture. Typically, however the drug is added before curing.

Although the tackifying resin is usually provided in the first step of the process, it may be provided in subsequent steps. Further, it is usually the case that a catalyst is provided in either the first, second or third step of process. When the catalyst is added in the second step, this is typically done after the drug for delivery to the skin has been added and typically after any additional additives have been incorporated. It is typically the case that the catalyst is added either at the end of the second step or beginning of the third step. Typically, the catalyst promotes silanol condensation. Typical catalysts include, but are not limited to; organic derivatives of titanium (III), titanium (IV) or aluminium (III), such as aluminium trisacetylacetonate, titanium tetraalkoxides such as titanium tetrabutoxide and titanium tetraethoxide; and amines, such as 1,8-diazobicyclo[5.4.0]undec-7-ene.

The third step of curing the polymer is typically done in a humid environment i.e. in the presence of water. According to one embodiment, the composition is cured in a humid atmosphere characterized by its humidity level. The humidity level is typically controlled by an appropriate device typically comprising a humidity generator, sensor and regulatory system. Examples of suitable devices are described for instance in EP 2856 937. Typically, the humidity of the curing step is such that in the range of 1% to 100% of the molecules in the curing atmosphere are water, more typically in the range 2% to 95%, more typically still 5% to 90% and even more typically in the range 10% to 80%, even more typically still 15% to 70%. It is often the case that the humidity is in the range 20% to 50% or even more typically still in the range of 25% to 40%. In some case, the humidity is in the range of 1% to 90%, often 1% to 10% and in some cases 2% to 8%.

The second step may include heating the first component to a temperature in the range 30 to 150° C., typically 50 to 130° C. and most typically 70 to 100° C.

The second step of the process typically includes a mixing step in order to assist dissolution of the drug and ensure a homogeneous mixture is obtained. This may be done with one or more solvents or co-solvents in order to improve dissolution of drugs into the first component. The solvents and co-solvents suitable for use are described above. Typically, said solvents are substantially free of water to prevent any premature curing.

In addition, preservatives, excipients and other additives may be added to the composition and this is typically done together with the addition of the drug, typically during the second step. The first and/or second step may be conducted in an inert atmosphere.

The curing step is typically performed at a temperature greater than room temperature, typically greater than 20° C., often in the range 20 to 200° C. and more typically in the range 40 to 120° C. Often, the temperature will be in the range 50 to 80° C. and is most typically around 60° C. A catalyst is typically employed. However, as will be appreciated, lowers temperature may be used if a catalyst is provided.

Typically, in the second step, once a substantially homogeneous mixture has been obtained, the mixture is applied to a back liner or releasable liner before curing. Typically the mixture is formed into a layer and may be sandwiched between two back liners or releasable liners or combination thereof. There is no particular restriction on the shape or material of the back liner or releasable layer. The back liner is typically a thin, flexible material usually having a thickness of less than 5 mm and often less than 1 mm. The back liner typically bonds strongly to the composition layer. Typically, examples of releasable materials include siliconised surfaces; polyolefinic films or coatings, such as high density polyethylene or polypropylene; stretchable or deformable films or coatings, such as fluoro silicones or polytetrafluoroethylene; and acetate sheeting.

Although it is typically the case that the drug for drug delivery to the skin is introduced before the composition has been cured, depending on the thermal and chemical stability of the drug to be delivered, the drug may be incorporated after the composition has been cured. The drug may be a solid, liquid or a solution comprising the drug when added to the composition.

There is no particular limitation on the duration of the curing step. The time needed for the curing step may vary to a large extent depending on the weight per unit area of composition deposited on the substrate, on the heating temperature, the humidity and the particular makeup of the composition in question. Typically, the duration of the curing steps is in the range of 1 second to 24 hours and more typically is in the range 5 minutes to 24 hours. However, with the silyl-containing polymers of the present invention, curing times can be in range 2 minutes to 30 minutes, more typically 5 to 15 minutes and in many cases less than about 10 minutes or less.

Without being bound by theory, it is believed that this curing step has the effect of creating between the polymer chains, under the action of atmospheric moisture, siloxane-type bonds which result in the formation of a three-dimensional polymer network. The thus cured composition acts as a pressure-sensitive adhesive layer which gives the substrate that is coated therewith desirable adhesive strength and tack.

The process may be a batch process or a continuous process. A continuous process may involve the use of heated rollers and to form and heat the composition and steam jets sprinklers may be used to provide humidity to promote the cross-linking reaction.

There is provided in a third aspect of the invention, use of a composition as described above as pressure sensitive adhesives and more typically for transdermal drug delivery.

The inventors have found that compositions comprising the cross-linked silyl-containing polymer are extremely effective as adhesives and at storing and conveying drugs to the skin. This is particularly the case when combined with a tackifying resin as described above which helps adherence to the skin.

The composition implemented in the use according to the third aspect of the invention is typically a drug delivery patch. Typically a patch for drug delivery to the skin.

Typically, the drugs used in the composition of the third aspect of the invention are as described above.

There is provided in a fourth aspect of the invention, a method of treating a disease comprising; providing a composition or patch as described above; and applying the composition or patch to a user. Typically, to a user's skin.

There is no particular limitation on the types of disease that can be treated using this method. The only limitation is that the drugs used to treat a particular condition are effective when administered to the skin. Typical applications for the composition of the invention include the treatment of diseases selected from: analgesia; hypertension; addiction e.g. to nicotine; hormone imbalance; cancer, such as skin cancer; bacterial, viral or fungal infections, Alzheimer's disease, mood disorders, Parkinson's, metabolic diseases, tissue scarring or combinations thereof.

Further, the method of treatment of the invention may also be for delivering vaccines and/or for improving wound healing.

There is also provided in a fifth aspect of the invention a composition or patch according to the first aspect of the invention for use in therapy. Typically, the conditions which can be treated with the composition or patches of the invention are: analgesia; hypertension; addiction e.g. to nicotine; hormone imbalance; cancer, such as skin cancer; bacterial, viral or fungal infections, Alzheimer's disease, mood disorders, Parkinson's, metabolic diseases, tissue scarring or combinations thereof. Most typically, the compositions and patches of the invention are for use in treating analgesia.

Further, the composition and patches of the invention may also be used as a means for delivering vaccines and/or as a means to improve wound healing.

The invention will now be described with reference to the following figures and examples.

EXAMPLES

Example 1—Peel Adhesion Properties

Figure 1:
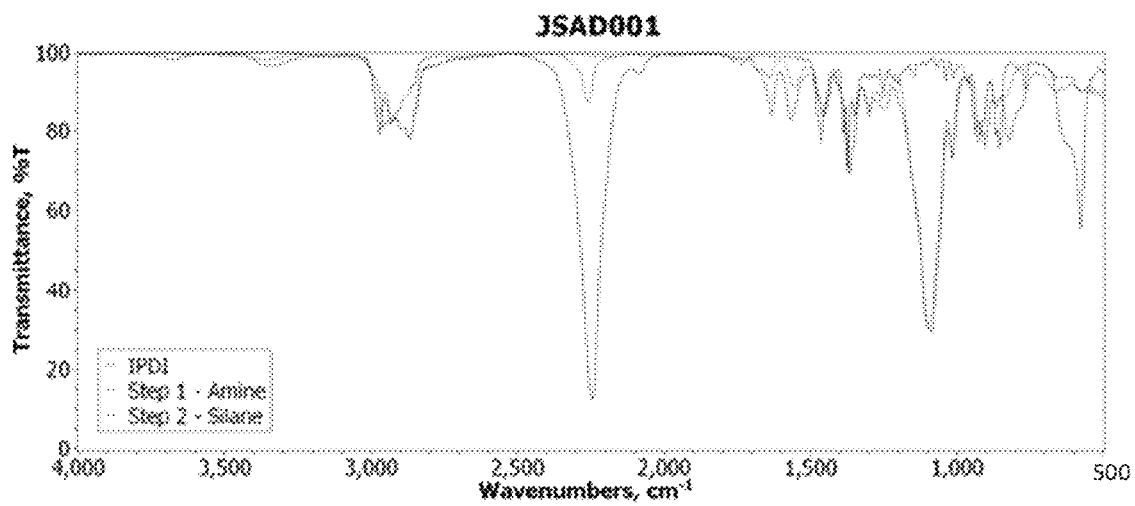
FIG. 1 shows to an IR spectra of the formation of JSAD001 with reference to the reduction in the IR peak associate with isocyanate groups.

| Sample Code | Adhesive | Mass | Adhesive | Ti(iv) Catalyst | DEGEE | API |
|---|---|---|---|---|---|---|
| JSAD001A Ibuprofen | JSAD001A 110518 | actual, g weight % | 8.94 91 | 0.295 3 | 0.491 5 | 0.0982 1 |
| JSAD001A Lidocaine | JSAD001A 110518 | actual, g weight % | 8.2 96 | 0.256 3 | | 0.0854 1 |
| JSAD001A Nicotine | JSAD001A 110518 | actual, g weight % | 5.21 92 | 0.17 3 | | 0.2832 5 |
| JSAD002A Ibuprofen | JSAD002A 220518 | actual, g weight % | 8.41 87 | 0.29 3 | 0.4833 5 | 0.4833 5 |
| JSAD002A Lidocaine | JSAD002A 220518 | actual, g weight % | 10.05 92 | 0.328 3 | | 0.5462 5 |
| JSAD002A Methyl Salcylate | JSAD002A 220518 | actual, g weight % | 8.85 92 | 0.289 3 | | 0.481 5 |
| JSAD002A Diclofenac | JSAD002A 220518 | actual, g weight % | 9.52 82 | 0.348 3 | 1.161 10 | 0.2902 2.5 |
| JSAD003A Ibuprofen | JSAD003A 230518 | actual, g weight % | 6.27 87 | 0.216 3 | 0.3603 5 | 0.3603 5 |
| JSAD003A Lidocaine | JSAD003A 230518 | actual, g weight % | 7.32 92 | 0.239 3 | | 0.3978 5 |
| JSAD003A Methyl Salcylate | JSAD003A 230518 | actual, g weight % | 8.14 92 | 0.265 3 | | 0.4424 5 |

The peel adhesion properties of compositions of the present invention were tested against polyol polyurethane equivalents. The peel test is based on FINAT No 2 90° Peel Test and ASTM 3330-34 (2010) for testing adhesive tapes on stainless steel using a speed of 100 mm/min. The results of these test is shown below in Table 1.

TABLE 1

Peel Adhesion

| No. | Composition | Drug | Max Peel/ N | Average/ N |
|---|---|---|---|---|
| Comp Ex. 1 | polyurethane polyol/ tackifying resin (50:50) | No Drug Ibuprofen (ITP10-0.150.2) Lidocaine LTP.F01 Diclofenac DTP.F07 | — 4.50 (0.84) 8.60 (1.00) 2.40 (0.10) | 9.22 1.38 (0.13) 7.70 (0.13) 1.80 (0.60) |
| JSAD001 | Polyurea polyol/ tackifying resin (75:25) | No Drug Ibuprofen Lidocaine Nicotine | 2.20 (0.11) 8.54 (0.31) 6.26 (0.16) 5.82 (0.40) | 1.88 (0.08) 7.39 (0.33) 5.66 (0.18) 5.00 (0.38) |
| JSAD002 | Polyurea polyol/ tackifying resin (50:50) | Ibuprofen Lidocaine Methylsalicylate Diclofenac | 14.10 (4.43) 1.99 (0.05) 2.04 9.88 (0.47) | 13.80 (4.35) 1.96 (0.03) 1.97 9.43 (0.68) |
| JSAD003 | Polyurea polyol/ tackifying resin (75:25) | Ibuprofen Lidocaine Methylsalicylate | 0.57 (0.10) 1.81 (0.23) 1.29 (0.08) | 0.56 (0.09) 1.73 (0.22) 0.99 (0.02) |

Average (std dev)

Reference in table 1 to compositions using "no drug" can be considered as describing adhesive compositions.

Example 2—Ibuprofen Release

The ibuprofen release properties of compositions of the present invention were tested against polyol polyurethane equivalents. The results of these tested is shown below in Table 2.

TABLE 2

Ibuprofen Release

| No. | Composition | Time/ hrs | Amount/ μg cm$^{-2}$ | Flux/ μg cm$^{-2}$ hr$^{-1}$ |
|---|---|---|---|---|
| Comp Ex. 1 | polyurethane polyol/ tackifying resin (50:50) | 1 2 4 6 | 227.93 438.23 726.09 967.49 | 227.93 210.3 143.93 120.7 |
| JSAD001 | Polyurea polyol/ tackifying resin (75:25) | 1 2 4 6 | 104.03 175.61 252.1 47.08 | 104.03 71.58 38.25 77.49 |
| JSAD002 | Polyurea polyol/ tackifying resin (50:50) | 1 2 4 6 | 131.12 163.75 252.73 290.6 | 131.12 32.63 44.49 18.94 |
| JSAD003 | Polyurea polyol/ tackifying resin (75:25) | 1 2 4 6 | 136.39 147.3 226.49 272.48 | 136.39 10.91 39.6 22.99 |

Example 3—Lidocaine Release

The Lidocaine release properties of compositions of the present invention were tested against polyol polyurethane equivalents. The results of these tested is shown below in Table 3.

TABLE 3

Lidocaine Release

| No. | Composition | Time/ hrs | Amount/ μg cm$^{-2}$ | Flux/ μg cm$^{-2}$ hr$^{-1}$ |
|---|---|---|---|---|
| Comp Ex. 1 | polyurethane polyol/ tackifying resin (50:50) | 1 2 4 6 | 181.77 96.24 412.89 505.82 | 212.06 133.55 68.05 54.21 |
| JSAD001 | Polyurea polyol/ tackifying resin (75:25) | 1 2 4 6 | 189.55 289.33 454.05 547.48 | 189.55 99.78 82.36 46.72 |
| JSAD002 | Polyurea polyol/ tackifying resin (50:50) | 1 2 4 6 | 235.56 305.36 476.29 578.63 | 235.56 69.8 85.46 51.17 |

Example 4—Methyl Salicylate Release

The methyl salicylate release properties of compositions of the present invention were tested against polyol polyurethane equivalents. The results of these tested is shown below in Table 4.

TABLE 4

Methyl Salicylate Release

| No. | Composition | Time/ hrs | Amount/ μg cm$^{-2}$ | Flux/ μg cm$^{-2}$ hr$^{-1}$ |
|---|---|---|---|---|
| Comp Ex. 1 | polyurethane polyol/ tackifying resin (50:50) | 1 2 4 6 | 12.89 20.81 26.81 34.52 | 15.04 9.23 3.5 4.5 |
| JSAD001 | Polyurea polyol/ tackifying resin (75:25) | 1 2 4 6 | 0.61 0.51 0.77 0.94 | 0.61 −0.1 0.13 0.08 |
| JSAD002 | Polyurea polyol/ tackifying resin (50:50) | 1 2 4 6 | 19.63 40.12 73.53 60.14 | 19.63 20.49 16.7 −6.7 |

Example 5—Diclofenac Release

The Diclofenac release properties of compositions of the present invention were tested against polyol polyurethane equivalents. The results of these tested is shown below in Table 5.

TABLE 5

Diclofenac Release

| No. | Composition | Time/ hrs | Amount/ μg cm$^{-2}$ | Flux/ μg cm$^{-2}$ hr$^{-1}$ |
|---|---|---|---|---|
| Comp Ex. 1 | polyurethane polyol/ tackifying resin (50:50) | 1 2 4 6 | 37.78 77.7 150.06 211.45 | 44.08 46.57 42.21 35.81 |
| JSAD002 | Polyurea polyol/ tackifying resin (50:50) | 1 2 4 6 | 16.18 29.79 53.37 85.96 | 16.18 13.61 11.79 16.3 |

Example 6—Method of Manufacture

Synthesis of JSAD001

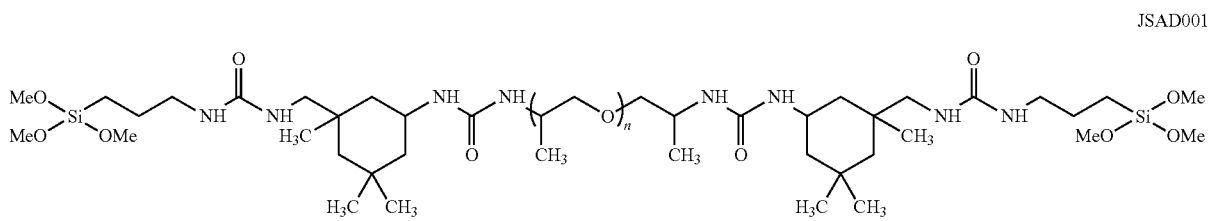

JSAD001

Step 1-Isophorene Diisocyanate (IPDI) (2.27 g, 2.05 eq) heated to 60° C. with stirring, Jeffamine D-4000 (Mw=4000 Da, NH$_2$ functionality=2) (20.0 g, 1 eq) added dropwise to isocyanate and stirred at 60° C. for 5 min. No catalyst is required and IR data shows reaction complete after 5 min as reduction in NCO peak at ≈2240 cm$^{-1}$ (see FIG. 1), longer reaction times do not decrease this peak further than at 5 min.

Reaction of step 1 is possible at room temp but higher temperature used to reduce viscosity and improve mixing.

Step 2—3-aminopropyl trimethoxysilane (2.38 g, 2.05 eq) added to reaction mixture at 60° C. and stirred for 10 min. Reaction monitored for disappearance of NCO peak which occurs at 10 min.

Synthesis of JSAD002

Step 1—IPDI (1.71 g, 1.53 eq) stirred at 60° C., Jeffamine D-4000 (20.0 g, 1.0 eq) added dropwise and stirred for 5 min.

Step 2—3-aminopropyl trimethoxysilane (1.70 g, 1.53 eq) added to reaction and stirred for 10 min.

Synthesis of JSAD003

Step 1—IPDI (2.39 g, 1.53 eq) heated to 60° C., Jeffamine D-4000 (14.0 g 0.5 eq) and Jeffamine D-2000 (Mw=2000 Da, NH$_2$ functionality=2) (7.0 g, 0.5 eq) mixed and added dropwise to the isocyanate and stirred for 5 min.

Step 2—3-aminopropyl trimethoxysilane (2.38 g, 1.53 eq) added to reaction and stirred for 10 min.

Synthesis of JSAD005.3

Synthesis of JSAD006

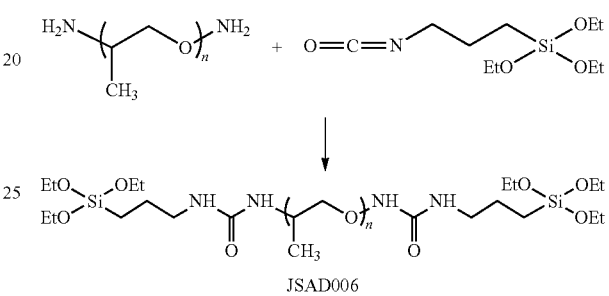

JSAD006

Step 1—(3-Isocyanatopropyl) triethoxysilane (1.903 g, 2.05 eq) added dropwise to Jeffamine D-4000 (15 g, 1 eq) at 60°, reaction complete in 5 min.

Example 7—Curing Process

To formulate an adhesive (e.g. JSAD002A) the base polymer (e.g. JSAD002) was mixed with a resin solution. The resin solution contained Norsolene W110 and Sylvalite RE100s in a 50:50 ratio dissolved in MEK (e.g. 66.2% solid content). The resin solution was mixed with the polymer and MEK removed by rotary evaporation to give an equal mass

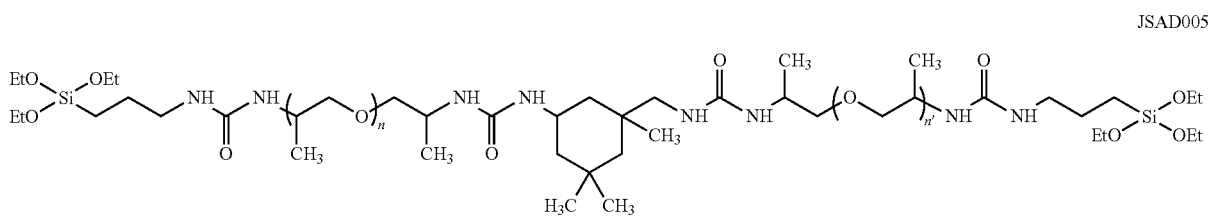

JSAD005

Figure 2:
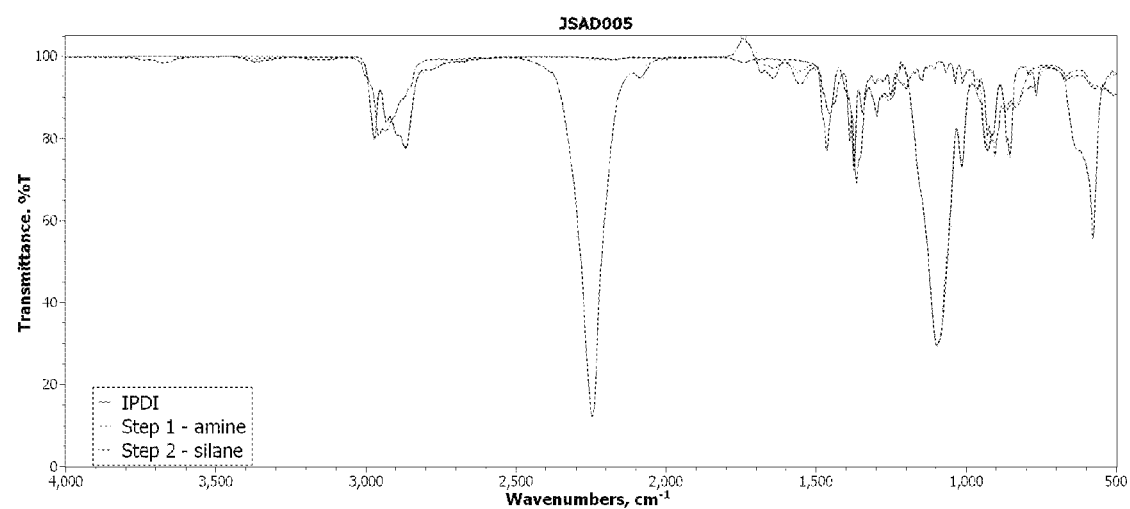
FIG. 2 shows to an IR spectra of the formation of JSAD005 with reference to the reduction in the IR peak associate with isocyanate groups.
Figure 3:
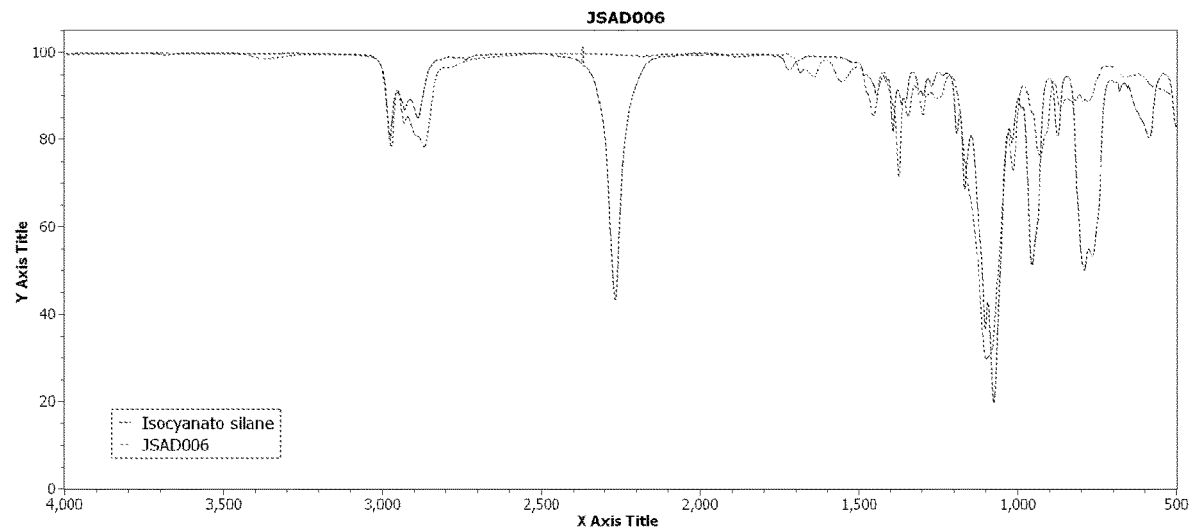
FIG. 3 shows to an IR spectra of the formation of JSAD006 with reference to the reduction in the IR peak associate with isocyanate groups.
Figure 4:
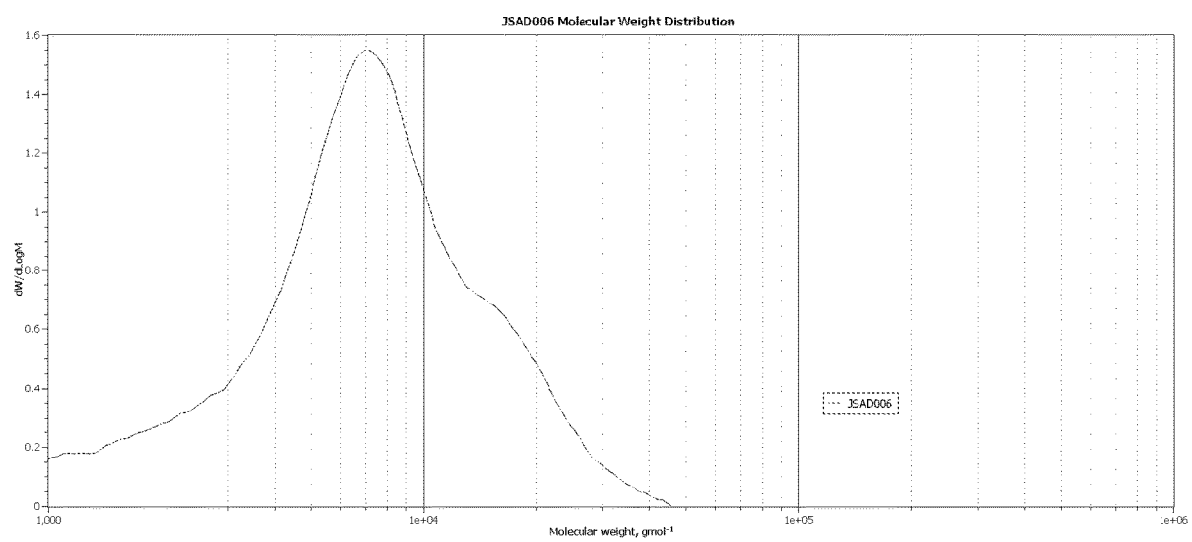
FIG. 4 shows the molecular weight distribution of JSAD006.

Step 1—Jeffamine D-4000 (10.0 g, 1 eq) heated to 60° C., IPDI (0.285 g, 0.51 eq) added dropwise and reaction stirred at 60° C. for 5 min monitored by complete reduction of NCO peak at 2240 cm$^{-1}$ (see FIG. 2).

Step 2—(3-Isocyanatopropyl) triethoxysilane (0.325 g, 0.51 eq) added to reaction mixture and stirred for 10 min.

Further reactions show that either adding amine to isocyanate or adding isocyanate to amine does not affect the molecular weight distribution.

fraction of resin to polymer—e.g 2.57 g JSAD002 mixed with 4.195 g resin solution (1.285 g Sylvalite, 1.285 g Norsolene. 1.625 g MEK).

To cure the patches the adhesive formulation was heated to 75° C., any API's and/or excipients are then added and allowed to fully mix/homogenise. The curing catalyst was then added (e.g. 7.17 g, 97 wt %, JSAD002A is mixed with 0.1109 g, 3 wt %, Ti(iv)butoxide). The catalyst was mixed for 5 min at 75° C. and the formulation cast onto a heated bed coater, a film was drawn at 30 microns thickness, steam was generated and contained in a chamber over the heated bed until curing complete.

The invention claimed is:

1. A composition for use in drug delivery comprising a crosslinked silyl-containing polymer, and one or more drugs, the polymer obtained by polymerising:
a first difunctional compound;
a second difunctional compound; and
a silyl containing compound comprising silyl groups,
wherein at least one of the first and second difunctional compounds together comprise a terminal amine group and a terminal isocyanate group that react to form urea linkages, wherein the first or second difunctional compound comprising the terminal amine group is polymeric, having a molecular weight in the range of from about 500 Dalton to about 10,000 Dalton, wherein the first or second difunctional compound comprising the terminal isocyanate group is monomeric, and
wherein the first and second difunctional compounds have structures according to Formula III and IV respectively:

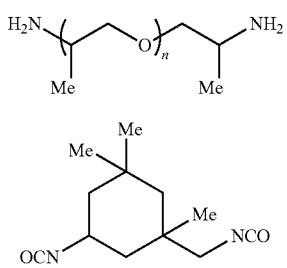

Formula III

Formula IV wherein n is an integer in the range of from about 20 to about 200,
wherein silyl groups of adjacent silyl containing polymers form cross-links between adjacent silyl containing polymers,
wherein the silyl containing compound is represented by a Formula V:

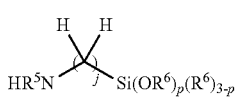

Formula V wherein:

p is an integer between 3 and 0;

$R^5$ is independently selected from: H, alkyl, alkenyl, aryl, heteroalkyl, heteroalkenyl, heteroaryl and cycloalkyl;

$R^6$ is $C_1$-$C_{10}$ alkyl; and j is an integer between 1 and 10.

2. The composition of claim 1, wherein the first and second difunctional compounds are polymerised in the absence of a catalyst.

3. The composition of claim 1, wherein the silyl-containing polymer is terminated with one or more silyl groups.

4. The composition of claim 1, further comprising a tackifying resin.

5. The composition according to claim 1, wherein the drug is selected from: nicotine, ibuprofen, meloxicam, olanzapine, memantine, donepezil, dronabinol, lidocaine, fentanyl, diclofenac, methyl salicylate, testosterone, luflunomide, terflunomide, apomorphine, ketamine, esketamine, amitriptyline, aripiprazole, colchicine, hydrocortisone, lamotrigine, loratadine, ketoprofen, naltrexone, ketorolac, granisetron, celecoxib, fulvestrant, indomethacin, agomelatine, escitalopram, fulvestrant, flurbiprofen, galantamine, methyl phenidate, mometasone, propafenone, clobazam, pramipexole, ropinirole, bisoprolol, levonorgestrel, ziprasidone, verapamil, meurafenib, propylthiouracil, methotrexate, pazopanib, maraviroc, lithium, lisdexamfetamine, huperazine a, calcitrol, temazolamib, bupropion, domperidone, lurasidone, tertracycline, progesterone, prilocaine, ivermectin, cannabidiol, artesunate, artemisinin, salsalate, buprenorphine, clobetasone butyrate, clonidine, dexamethasone, diflucortalone valerate, estradiol, oestrogen, ethinylestradiol, gestodene, norelgestromin, norethisterone, prednisolone, teriparatide, triamcinolone.

6. The composition according to claim 1, wherein the drug is selected from donepezil, testosterone, loratadine, progesterone, oestrogen.

7. The composition according to claim 6, comprising donepezil, testosterone, loratadine, progesterone, oestrogen, or combinations thereof, for use in treating hormone imbalance or Alzheimer's disease.

* * * * *